United States Patent [19]

Aikins

[11] Patent Number: 5,326,363
[45] Date of Patent: Jul. 5, 1994

[54] PROVISIONAL IMPLANT
[75] Inventor: Jerry L. Aikins, Warsaw, Ind.
[73] Assignee: Zimmer, Inc., Warsaw, Ind.
[21] Appl. No.: 944,856
[22] Filed: Sep. 14, 1992
[51] Int. Cl.⁵ .......................... A61F 2/38; A61B 5/103
[52] U.S. Cl. ........................................ 623/20; 623/18; 623/66; 128/782
[58] Field of Search ...................... 623/16, 18, 20, 66; 128/774, 782; 33/512, 645

[56] References Cited
U.S. PATENT DOCUMENTS 4,566,193 1/1986 Hackleman et al. .................. 33/645
5,086,785 2/1992 Gentile et al. ....................... 128/782
5,197,488 3/1993 Kovacevic ........................... 623/20

OTHER PUBLICATIONS

Tekscan, Inc.-Product Description-Copyright 1989.

Primary Examiner—David Isabella
Attorney, Agent, or Firm—Cary R. Reeves

[57] ABSTRACT

A provisional implant includes an indicator of implant function. Alternating electrically conductive regions and electrically insulating regions on the surface of the provisional implant cooperate with an electrically conducting mating component to indicate when the mating component is in contact with each of the electrically conducting regions.

3 Claims, 4 Drawing Sheets

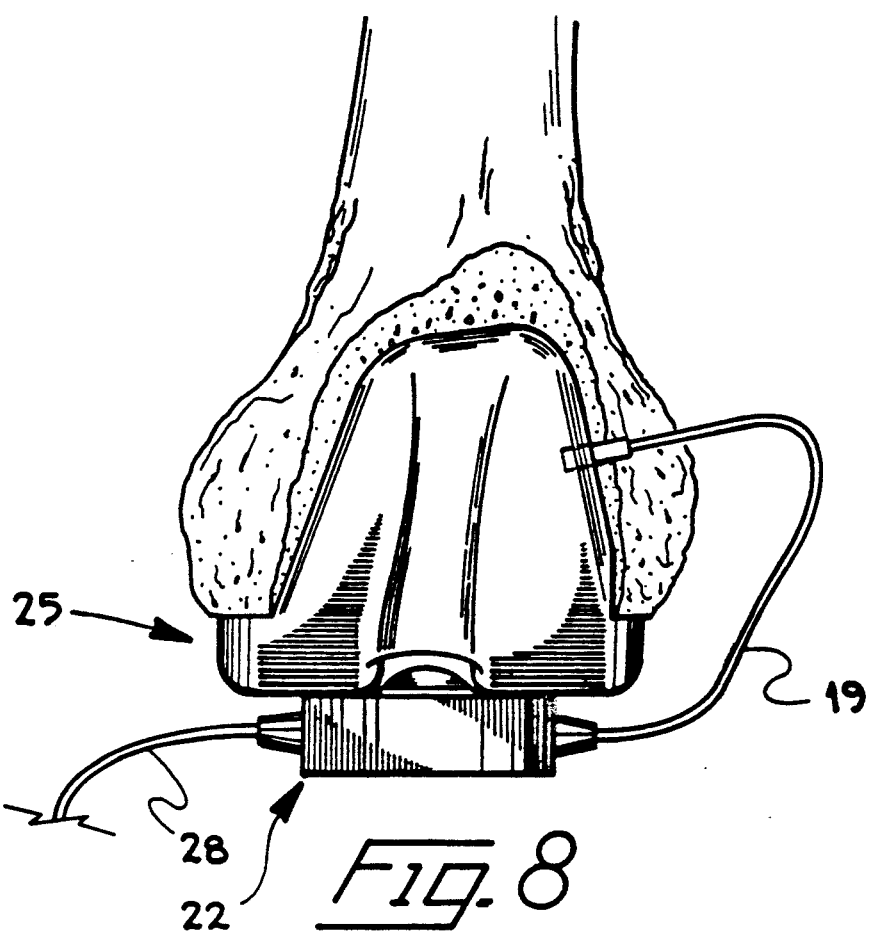
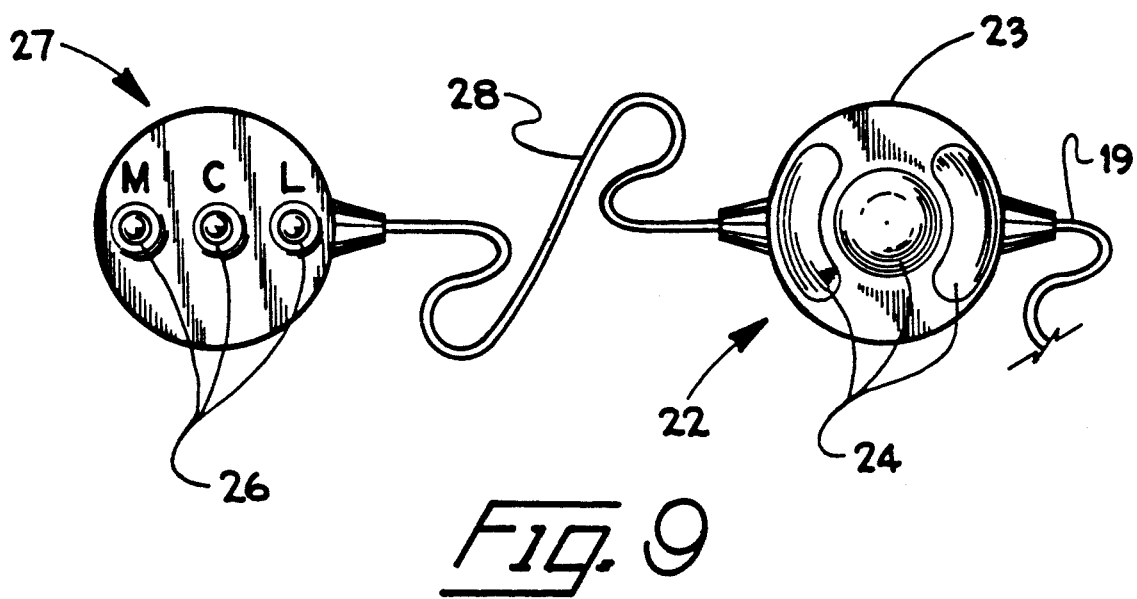

PROVISIONAL IMPLANT

BACKGROUND OF THE INVENTION

The present invention relates to provisional, or trial, implants having an indicator of implant function and joint kinematics.

During joint replacement surgery it is common for a surgeon to use a provisional implant or set of implants to determine the proper size and placement for a particular prosthetic joint component. Typically the affected bones are cut to accept the prosthetic component and then a succession of corresponding provisional components are tried in the joint. Each provisional is placed and its function and the joint kinematics are checked for such things as joint laxity or tightness, component tilt, and smoothness, freedom and extent of joint motion. With prior devices the surgeon has had to rely on his ability to sense or feel proper joint function and his ability to see in the indistinct environment of a surgical wound how the components are performing.

SUMMARY OF THE INVENTION

The present invention provides a positive indicator of implant function. Its design and method of indicating are straightforward and durable while the indication is easily interpreted. Furthermore, it is safe to both patient and surgeon. These features and benefits are provided by a provisional joint component having a functional surface of a generally nonconductive material interspersed with conductive regions. An electrical circuit is established when a conductive portion of a mating component contacts one or more of the conductive regions on the provisional component. The presence of a complete electrical circuit is displayed by an indicator, thus positively confirming the implant function.

BRIEF DESCRIPTION OF THE DRAWINGS

The before mentioned features and advantages of the present invention are apparent from the following detailed description and the drawings wherein:

FIG. 8 is a perspective view of a patellar embodiment of the invention.

FIG. 9 is a plan view of the embodiment of FIG. 8 also showing a separate indicator module.

DETAILED DESCRIPTION OF THE INVENTION

Figure 1:
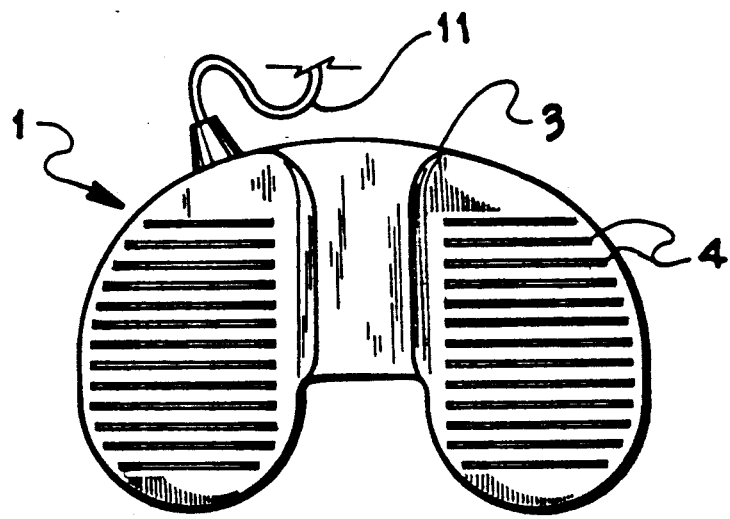
FIG. 1 is a plan view of an illustrative tibial provisional implant according to the invention.
Figure 2:
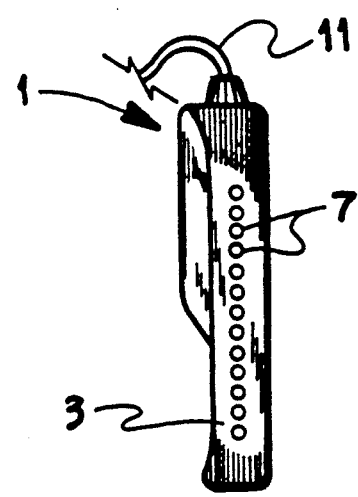
FIG. 2 is a side view of the provisional implant of FIG. 1.
Figure 3:
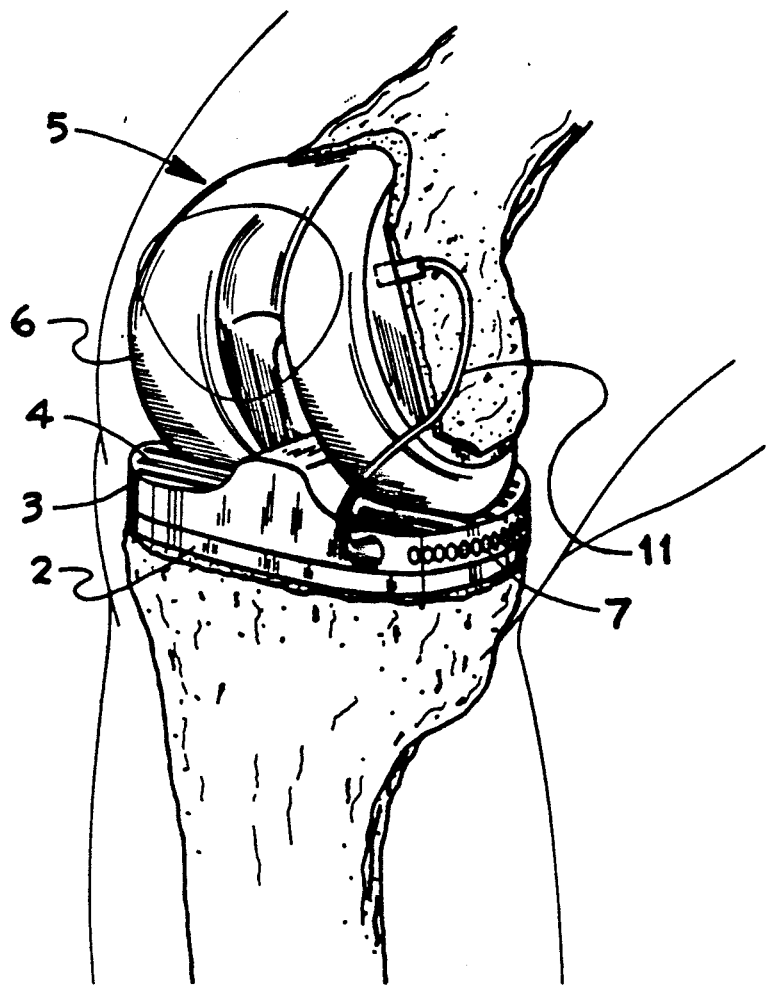
FIG. 3 is a perspective view of a human knee with the provisional implant of FIG. 1 and a femoral component in situ.
Figure 4:
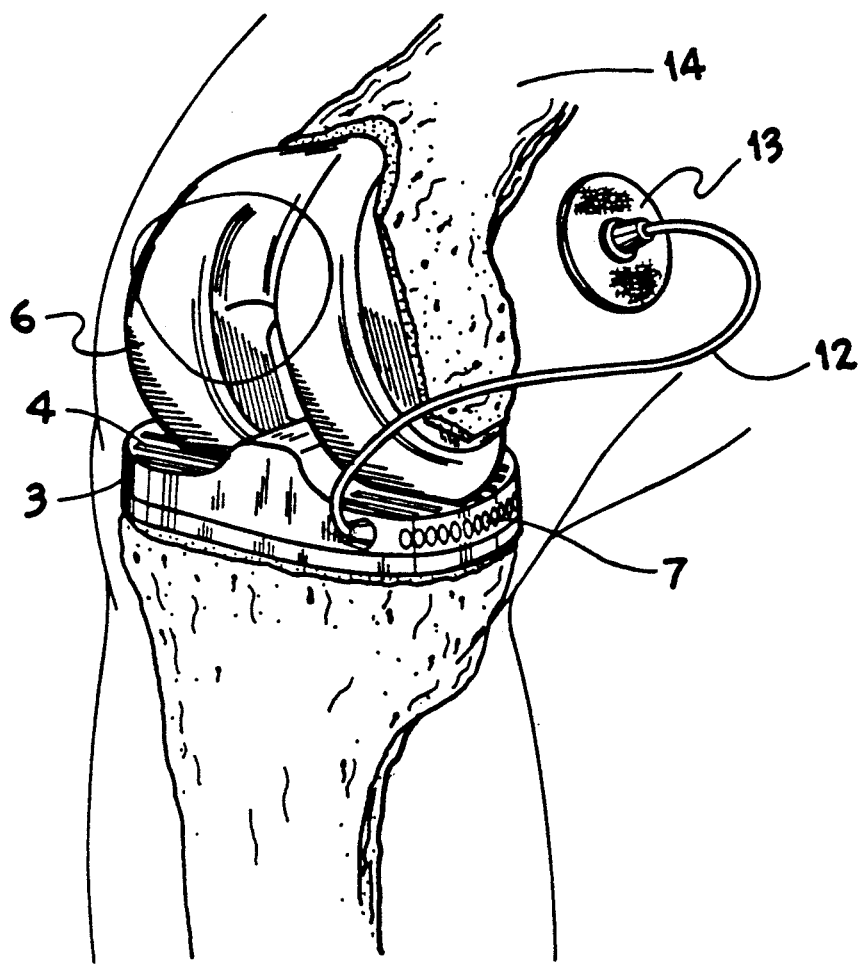
FIG. 4 is an alternative embodiment of the device depicted in FIG. 3.
Figure 5:
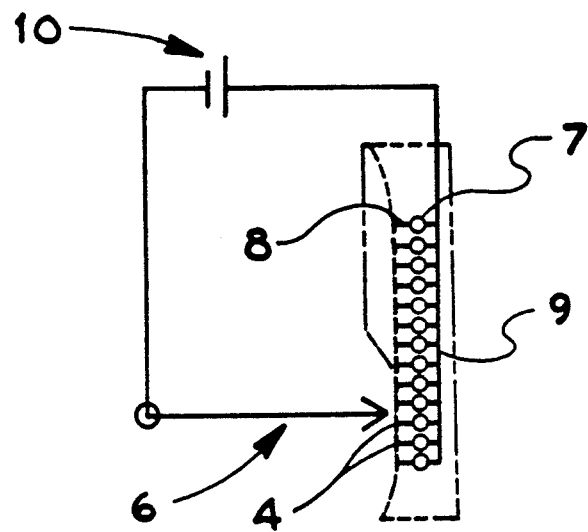
FIG. 5 is a schematic drawing of the components of FIG. 3.
Figure 6:
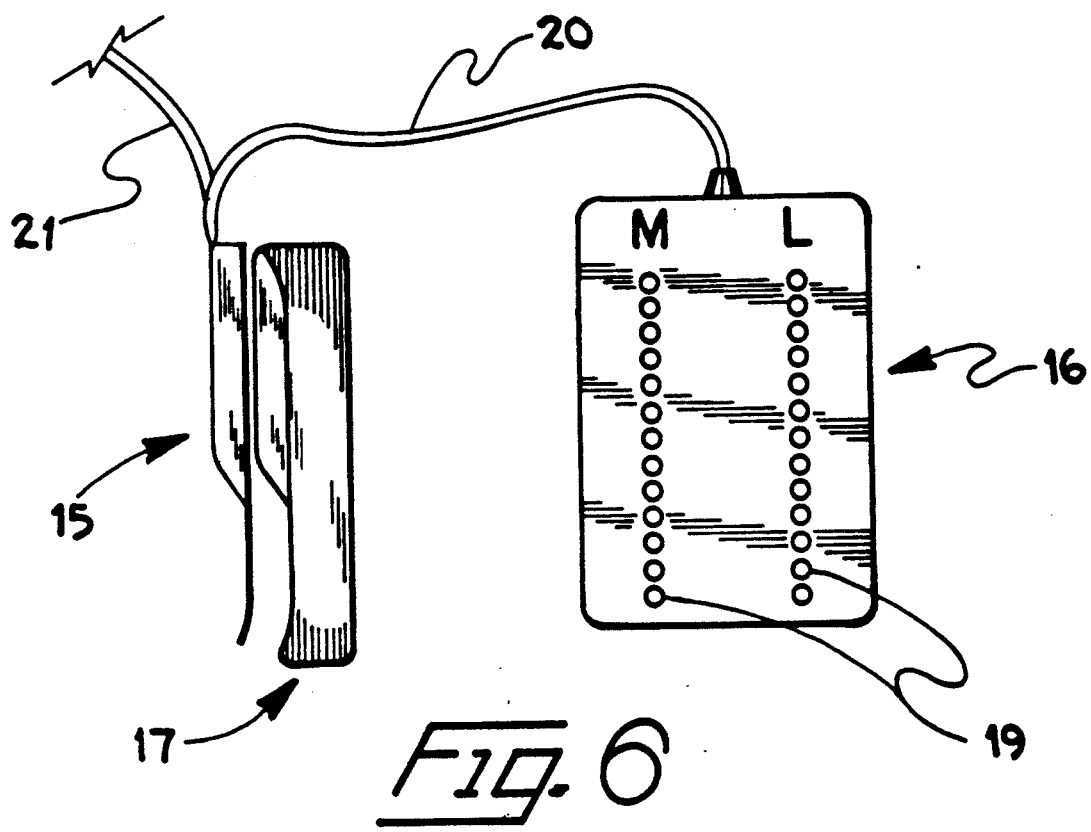
FIG. 6 is a side view of another tibial embodiment of the invention including a separate indicator module.
Figure 7:
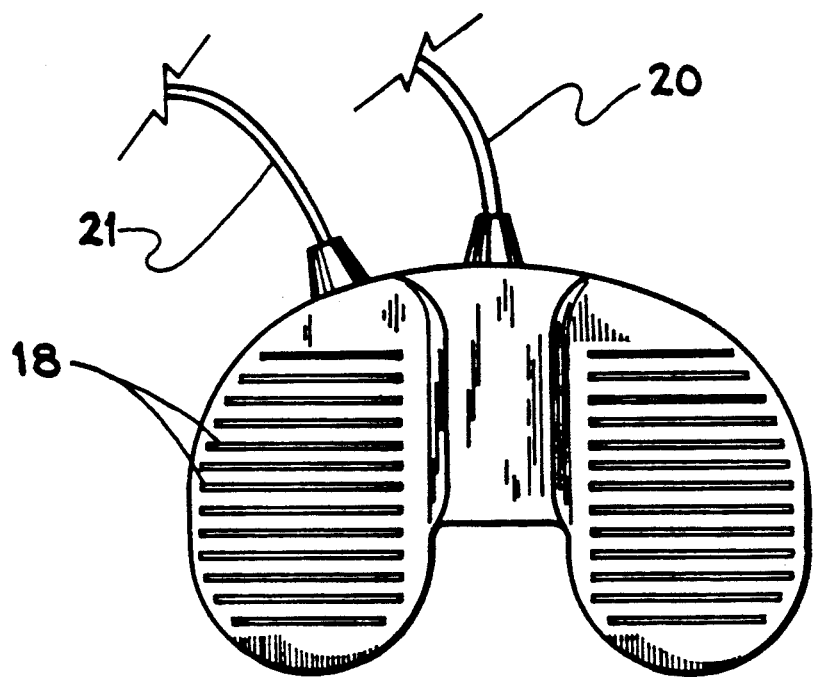
FIG. 7 is a plan view of the embodiment of FIG. 6 without showing the indicator module.

The desired end result of joint replacement surgery is the restoration of the joint to normal function. To achieve this result, surgeons match as closely as possible an appropriate implant to a patient's anatomy and condition. Then, while implanting the implant, the surgeon modifies the bone and soft tissue of the patient to accommodate the implant and to achieve normal joint function. As the surgeon progresses in the joint reconstruction, he periodically checks the joint function by placing a provisional implant in the prepared site and performing a trial reduction of the joint. With each joint of the body, there exist certain indications of normal function. In the knee joint for example, such an indication is rollback, the posterior movement of the tibiofemoral contact point with increasing flexion. While the normal amount of rollback varies from patient to patient, it is generally accepted that 5 to 10 mm of rollback occurs in the medial compartment of the knee and up to 20 mm of rollback can occur in the lateral compartment. This differential rollback between the compartments results in an internal rotation of the tibia during flexion in a normal knee. FIGS. 1 through 5 depict a provisional tibial articular surface, or tibial provisional 1, incorporating a means for intraoperatively assessing rollback. The tibial provisional 1 rests on and is supported by a base plate 2. The tibial provisional 1 comprises a body 3 of a non-conductive material having conductive regions 4 spaced on its articular surface such that when the tibial provisional articulates with a femoral component 5, a conductive surface 6 on the femoral component (depicted as switch 6 in FIG. 5) successively contacts the tibial conductive regions 4. An indicator for indicating contact between the femoral conductive surface 6 and the tibial conductive regions 4 is operatively associated with the tibial conductive regions and the femoral conductive surface. In one embodiment the indicator comprises a series of light emitting diodes 7 (L.E.D.s) mounted along each side of the tibial provisional, each L.E.D. having an electrical connection 8 to one of the conductive regions 4 on the tibial articular surface. Each L.E.D. is also connected to a common junction 9. A power source 10 connected between the common junction 9 and the conductive surface 6 of the femoral component 5 supplies power to light each L.E.D. as the L.E.D.'s corresponding conductive region contacts the femoral component. The power source could advantageously be located inside the provisional or in a separate power source module. Likewise, the means for indicating femoral contact could also be conveniently located in the separate module. A cable 11 connects the tibial provisional and the femoral component to complete the circuit. The alternative embodiment of FIG. 4 has a cable 12 connecting the tibial provisional to a conductive skin patch 13. In this embodiment, a completed circuit would include the conductive surface 6, a conductive region 4, an L.E.D. 7, common junction 9, power source 10, cable 12, conductive skin patch 13, and the patients skin and underlying tissue including the femur 14, which is electrically associated with conductive surface 6. By spacing the conductive regions an appropriate known distance, for instance 2 to 3 mm, the surgeon can readily determine the amount of rollback in each compartment by noting which L.E.D.'s are lit on each side of the provisional. The direction of the departure from normal kinematics can be noted and corrective action taken such as soft tissue release, implant repositioning, implant resizing, or other appropriate action. If, for example, the rollback indicator reads 6 mm of rollback medially and no rollback laterally, abnormal kinematics is established. The surgeon may execute a lateral release to gain more motion in the lateral compartment. Similarly, if, during repeated flexion and extension cycles, inconsistent readings are obtained, the surgeon may want to consider a thicker tibial articulating surface to reduce joint laxity. FIGS. 6 and 7 depict an embodiment of the invention which functions like the embodiment described above, but which structurally comprises a generally non-conductive thin substrate 15 and a separate indicator module 16. This embodiment would be adapted for use with a typical prior art provisional articular surface 17 in order to provide existing implant systems with the features of the present invention. The thin substrate 15 would fit closely and securely over the articular surface of the provisional component 17. It would include conductive regions 18. The indicator module 16 would include an indicator, such as a plurality of L.E.D.'s 19, for indicating joint function. The indicator module would advantageously contain the power source for the circuit. Cables 20 and 21 would connect the conductive regions 18 to the indicator module 16 and to the femoral component as previously described.

Another indication of normal joint function in the knee is whether and to what extent patellofemoral contact is being made on both medial and lateral condylar surfaces and on the patellar dome. If, in assessing patellar tracking intraoperatively, the patella tilts as the knee is flexed then the lateral retinacular pull on the patella may be overpowering the normal anterior-posterior patellofemoral joint load resulting from quadriceps function. This tilting generally indicates the need for a lateral retinacular release. FIGS. 8 and 9 depict a patellar provisional 22 incorporating a means for intraoperatively assessing patellar tilt. The patellar provisional 22 comprises a body 23 of a non-conductive material having conductive regions 24 spaced on its articular (posterior) surface such that when the patellar provisional 22 articulates with a femoral component 25, a conductive surface on the femoral component contacts the patellar conductive regions. The conductive regions are placed medially, laterally, and centrally. An indicator for indicating loss of contact due to patellar tilt between the femoral component and the patellar conductive regions is operatively associated with the patellar conductive regions and the femoral component. In one embodiment the indicator comprises a set of light emitting diodes 26 (L.E.D.s) mounted on an indicator module 27 separate from the patellar provisional, each L.E.D. being in electrical contact with a conductive region on the articular surface and also in contact with a common junction as described in the previous embodiment. A power source connected between the common junction and the femoral component will supply power to light each L.E.D. when the L.E.D.'s corresponding conductive region is in contact with the femoral component. This power source could be conveniently housed in the indicator module 27. A cable 28 connects the provisional 22 and the indicator module 27 to provide connections between the power source, L.E.D.'s and conductive regions. Another cable 19 connects the provisional to the conductive surface of the femoral component. By having the conductive regions in appropriate known locations the surgeon can readily determine where the patellar provisional is articulating and if it is tilted. The direction of the departure from normal kinematics can be noted and corrective action taken such as soft tissue release, implant repositioning, implant resizing, or other appropriate action. For example, if the L.E.D. on the lateral side of the patellar provisional is lit and the one on the medial side is not, then the surgeon knows that the provisional is articulating on the lateral portion of the femoral and is not making contact medially. Likewise, the central L.E.D. will indicate when the provisional is articulating on the patellar dome. Patellar tracking errors may be unnoticeable to the unaided surgeon. However, with the indicator disclosed above, the surgeon is able to correct slight patellar tracking errors and thereby improve the joint function and extend the service life of the patellar implant.

While the foregoing has described preferred embodiments of the present invention, variations in design and construction are possible. For example, various other joint replacement procedures would benefit from employing the present invention to provide an indicator of joint position, function and joint kinematics. These other procedures include replacements for total hips, bi-polar hips, shoulders, ankles and other joints. Also, the component having the spaced conductive regions and the one having the continuous conductive surface could be reversed in the illustrative embodiments and still function according to the invention. Also, the electrically conductive regions can comprise wires on the surface of the provisional body, metallic rails or bars embedded in the body, conductive ink or foil on the surface of the body, or other appropriate electrically conductive materials. The component surface may be permanently attached or removable and modular. For example, in the first tibial example, the power source and most of the circuitry could be located in the base plate 2, and the provisional 3 could be available in a variety of interchangeable thicknesses corresponding to available implants. In addition, the power source could be located in either component or in a separate module as discussed. It also could take the form of a battery, an alternating current converter, or other appropriate form. Finally, the indicator, while depicted as a series of L.E.D. 's could also take the form of incandescent bulbs, meters, color changing strips, cathode ray tube displays or a variety of other appropriate indicators with corresponding appropriate connections to the provisional..

It will be understood by those skilled in the art that the aforementioned modifications and numerous others may be made to the preferred embodiment without departing from the spirit and scope of the invention defined by the appended claims.

What is claimed is:

1. A system for determining joint function, the system comprising:
   a first prosthetic joint component having a first surface with a first electrically conductive region exposed thereon;
   a second prosthetic joint component engageable with the first member, the second member having a second surface with a second electrically conductive region exposed thereon and an electrically non-conductive region adjacent the second conductive region; and
   an indicator operatively associated with the second conductive region for indicating when the first conductive region makes electrical contact with the second conductive region, the second prosthetic joint component comprising a provisional joint replacement component having substantially the same size and shape as a corresponding component intended for permanent implantation.

2. A system for determining joint function, the system comprising:

a first prosthetic joint component having a first surface with a first electrically conductive region exposed thereon;

a second prosthetic joint component engageable with the first member, the second member having a second surface with a second electrically conductive region exposed thereon and an electrically non-conductive region adjacent the second conductive region; and an indicator operatively associated with the second conductive region for indicating when the first conductive region makes electrical contact with the second conductive region, the second prosthetic joint component comprising a provisional tibial component of an artificial knee having substantially the same size and shape as a corresponding component intended for permanent implantation;

the second surface comprising multiple, spaced metallic strips partially embedded in plastic;

the indicator comprising an electrical circuit containing light emitting diodes and a conductor connecting the circuit to the first member; and the first prosthetic joint component comprising a metallic femoral component such that when the first member articulates with the second member, the first conductive region contacts the metallic strips in a sequence determined by the particular motion produced by the joint's junction.

3. A system for determining joint function, the system comprising:

a first prosthetic joint component having a first surface with a first electrically conductive region exposed thereon;

a second prosthetic joint component engageable with the first member, the second member having a second surface with a second electrically conductive region exposed thereon and an electrically non-conductive region adjacent the second conductive region; and an indicator operatively associated with the second conductive region for indicating when the first conductive region makes electrical contact with the second conductive region the second prosthetic joint component comprising a provisional patellar component of an artificial knee having substantially the same size and shape as a corresponding component intended for permanent implantation;

the second surface comprising multiple, spaced metallic regions partially embedded in plastic;

the indicator comprising an electrical circuit containing light emitting diodes and a conductor connecting the circuit to the first member; and the first member comprising a metallic femoral component such that when the first member articulates with the second member, the first conductive region contacts the metallic regions in a sequence determined by the particular motion produced by the joint's function.

* * * * *